US011857204B2

(12) United States Patent
Windolf et al.

(10) Patent No.: US 11,857,204 B2
(45) Date of Patent: Jan. 2, 2024

(54) SURGICAL INSTRUMENT

(71) Applicant: SYNTHES GMBH, Oberdorf (CH)

(72) Inventors: Markus Windolf, Davos (CH); Viktor Varjas, Davos (CH); Peter Varga, Davos (CH)

(73) Assignee: Synthes GmbH

( * ) Notice: Subject to any disclaimer, the term of this patent is extended or adjusted under 35 U.S.C. 154(b) by 399 days.

(21) Appl. No.: 17/264,092

(22) PCT Filed: Jul. 22, 2019

(86) PCT No.: PCT/CH2019/000022
§ 371 (c)(1),
(2) Date: Jan. 28, 2021

(87) PCT Pub. No.: WO2020/024068
PCT Pub. Date: Feb. 6, 2020

(65) Prior Publication Data
US 2021/0307764 A1 Oct. 7, 2021

(30) Foreign Application Priority Data
Jul. 31, 2018 (CH) .................................. 00945/18

(51) Int. Cl.
*A61B 17/16* (2006.01)
*A61B 90/00* (2016.01)
*A61B 17/00* (2006.01)

(52) U.S. Cl.
CPC ...... *A61B 17/1626* (2013.01); *A61B 17/1628* (2013.01); *A61B 17/1633* (2013.01);
(Continued)

(58) Field of Classification Search
CPC . A61B 17/16; A61B 17/1613; A61B 17/1615; A61B 17/1617; A61B 17/162;
(Continued)

(56) References Cited

U.S. PATENT DOCUMENTS 6,033,409 A * 3/2000 Allotta .................... B25F 5/003
606/80
6,665,948 B1 * 12/2003 Kozin .................... A61B 90/06
175/45
(Continued)

FOREIGN PATENT DOCUMENTS

WO 2016/036756 A1 3/2016
WO 2017/083992 A1 5/2017

OTHER PUBLICATIONS

Ong F R et al: "Drilling of Bone: A Robust Automatic Method for the Detection of Drill Bit Break-Through", Proceedings of the Institution of Mechanical Engineers, Journal of Engineering in Medicine, Part H, Mechanical Engineering Publications Ltd, London, GB, vol. 212, No. H03, Jan. 1, 1998 (Jan. 1, 1998), pp. 209-221, XP000823771.

*Primary Examiner* — Eric S Gibson
(74) *Attorney, Agent, or Firm* — BakerHostetler

(57) ABSTRACT

A surgical instrument (25), in particular a surgical cutting or drilling instrument, the surgical instrument (25) comprising: a drive unit; a cutting tool or drill bit (5) engageable with the drive unit; a measuring device (1) which is configured to measure the distance [x(t)] covered by the cutting tool or drill bit (5) along a cutting or drilling path with respect to time and relative to a reference position; a processing un and a digital data storage, wherein in the digital data storage reference data are stored which include at least N one data set specifying a reference graph $G_{Ref}$ within a time window (11) in the range of a transition and defining a reference point of a transition (21'), wherein the time window (11) includes a first time period before the reference point of a transition (21') and a second time period after the reference point of a transition (21') and wherein the processing unit (14) suitably programmed to compare the recorded graph G (Continued)

with the at least one reference graph $G_{Ref}$ and to find 1 lion of a transition (21) in the recorded graph G.

60 Claims, 10 Drawing Sheets

(52) U.S. Cl.
CPC .... *A61B 90/06* (2016.02); *A61B 2017/00075* (2013.01); *A61B 2017/00115* (2013.01); *A61B 2017/00221* (2013.01); *A61B 2090/062* (2016.02); *A61B 2560/0223* (2013.01); *A61B 2562/0219* (2013.01)

(58) Field of Classification Search
CPC ............ A61B 17/1622; A61B 17/1624; A61B 17/1626; A61B 17/1628; A61B 17/1633
See application file for complete search history.

(56) References Cited

U.S. PATENT DOCUMENTS

| | | | |
|---|---|---|---|
| 8,821,493 B2 * | 9/2014 | Anderson | A61B 17/1633 606/171 |
| 8,894,654 B2 * | 11/2014 | Anderson | B23B 49/02 173/176 |
| 9,204,885 B2 * | 12/2015 | McGinley | A61B 17/162 |
| 9,358,016 B2 * | 6/2016 | McGinley | A61B 17/162 |
| 9,370,372 B2 * | 6/2016 | McGinley | A61B 17/1626 |
| 9,492,181 B2 * | 11/2016 | McGinley | A61B 17/162 |
| 9,826,984 B2 * | 11/2017 | McGinley | A61B 17/142 |
| 9,877,734 B2 * | 1/2018 | Anderson | B23B 45/008 |
| 10,149,686 B2 * | 12/2018 | Anderson | A61B 17/17 |
| 10,321,920 B2 * | 6/2019 | McGinley | A61B 17/1633 |
| 10,321,921 B2 * | 6/2019 | McGinley | A61B 17/1626 |
| 10,398,453 B2 * | 9/2019 | McGinley | A61B 90/30 |
| 10,736,644 B2 * | 8/2020 | Windolf | A61B 17/1615 |
| 10,893,873 B2 * | 1/2021 | McGinley | A61B 17/1626 |
| 10,925,619 B2 * | 2/2021 | Anderson | A61B 17/1628 |
| 11,000,292 B2 * | 5/2021 | McGinley | A61B 17/1633 |
| 11,058,436 B2 * | 7/2021 | McGinley | A61B 17/142 |
| 11,317,927 B2 * | 5/2022 | Carusillo | A61B 17/162 |
| 11,382,639 B2 * | 7/2022 | Miller | A61B 17/1624 |
| 11,478,255 B2 * | 10/2022 | Windolf | A61B 17/1615 |
| 2005/0131415 A1 * | 6/2005 | Hearn | B25B 23/147 606/80 |
| 2009/0245956 A1 * | 10/2009 | Apkarian | B23B 49/00 408/11 |
| 2009/0326537 A1 * | 12/2009 | Anderson | A61B 17/17 606/80 |
| 2011/0245833 A1 * | 10/2011 | Anderson | B23B 49/02 606/80 |
| 2014/0371752 A1 * | 12/2014 | Anderson | A61B 17/1624 606/80 |
| 2015/0066038 A1 * | 3/2015 | McGinley | A61B 17/1615 606/80 |
| 2015/0088183 A1 | 3/2015 | Vipperman et al. | |
| 2016/0128704 A1 * | 5/2016 | McGinley | A61B 17/17 606/86 R |
| 2017/0181753 A1 | 6/2017 | Langeland | |
| 2017/0348010 A1 * | 12/2017 | Chiang | A61B 90/03 |
| 2021/0307764 A1 * | 10/2021 | Windolf | A61B 17/1633 |

\* cited by examiner

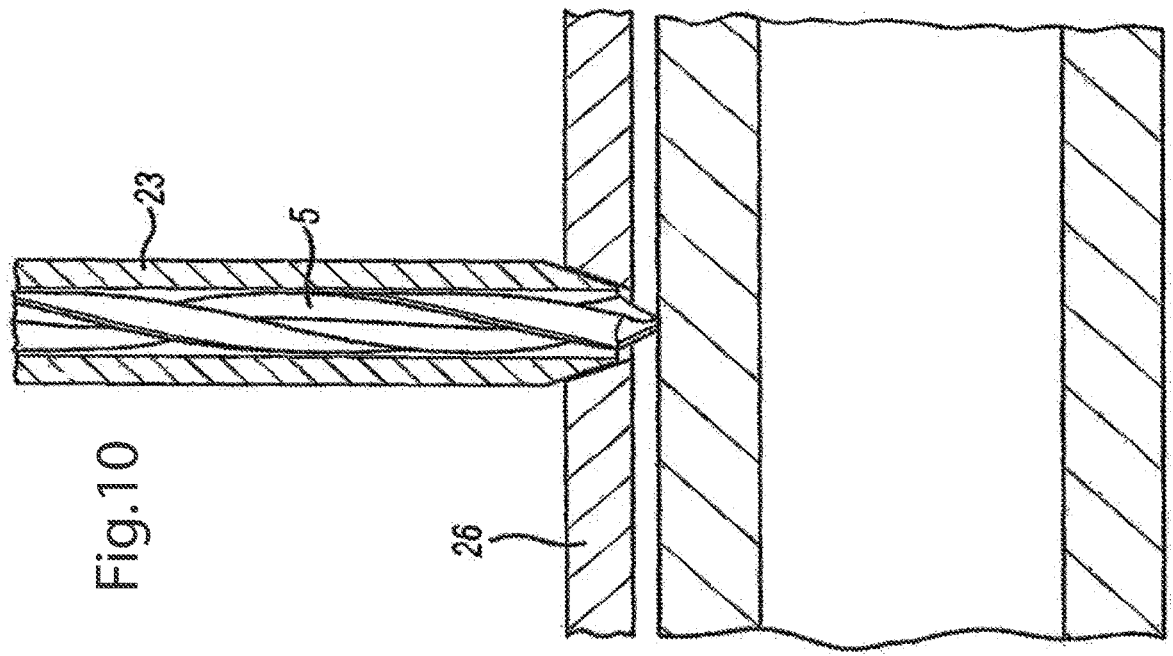
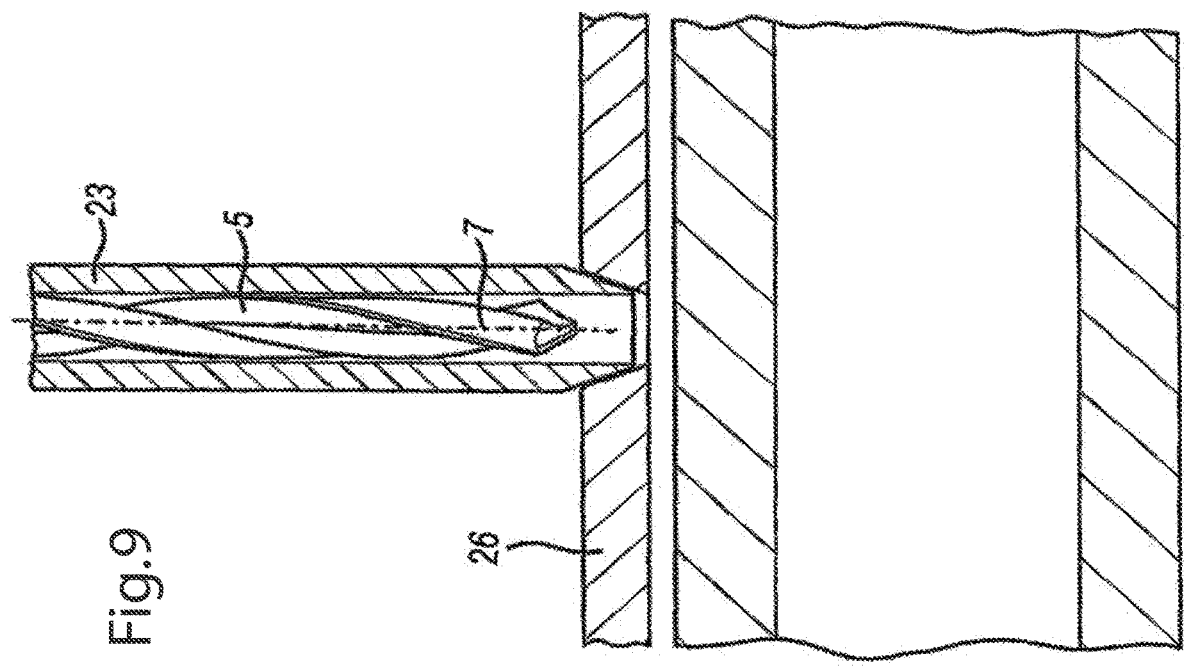

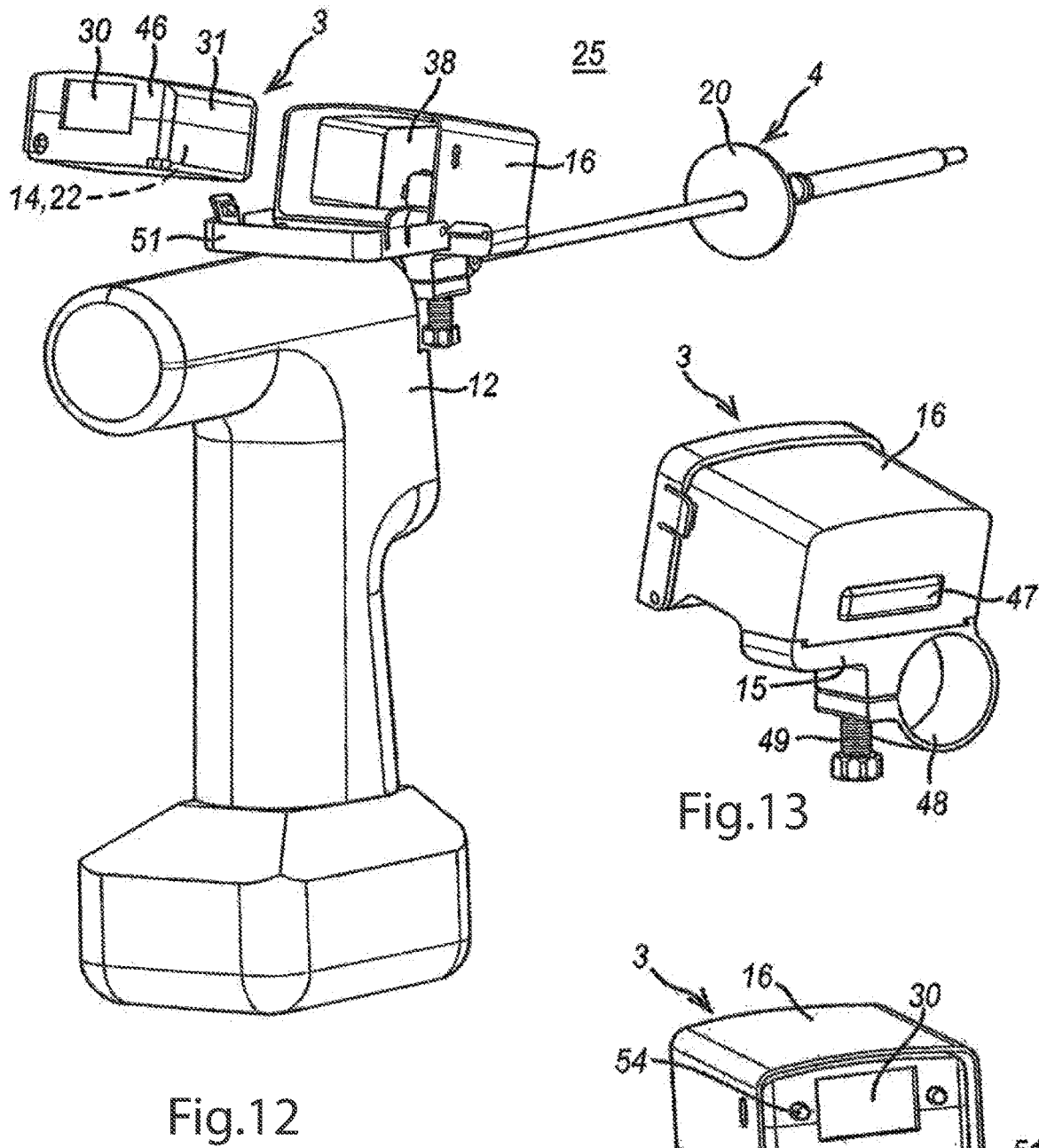
Fig.12
Fig.13
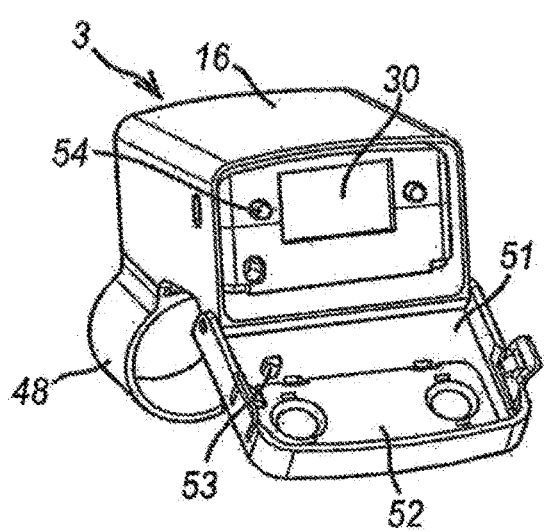
Fig.14

SURGICAL INSTRUMENT

CROSS-REFERENCE TO RELATED APPLICATIONS

This application is a National Stage Application filed Under 35 U.S.C. § 371 of International Application No. PCT/CH2019/000022 filed Jul. 22, 2019, which claims priority to CH00945/18 filed Jul. 31, 2018, which is hereby incorporated by reference in its entirety.

BACKGROUND OF THE INVENTION

1. Field of the Invention

The invention relates to a surgical instrument and a method for bone screw length estimation from drilling characteristics.

From clinical observations one problem in orthopedic and trauma surgery is the determination of the required screw lengths for e.g. bi-cortical screw placement before inserting a screw into a bone fragment. Current mechanical depths gauges are rather inaccurate, unreliable and difficult to handle resulting in:
- prolonged surgery time;
- insertion of too long screws resulting in soft tissue irritation, pain and re-operation;
- insertion of too short screws resulting in osteosynthesis failure, re-operation;
- need for exchange of screws resulting in screw scrap, increased hardware costs.

2. Description of the Related Art

A surgical power drill including an integrated measurement system for determining when the leading edge of a surgical tool passes from a first medium to a second medium is known from US 2016/036756 MCGINGLEY ET AL. This known power drill comprises a displacement sensor that outputs a displacement signal representative of a displacement of the leading edge of the tool relative to a reference point, a calculation module in operative communication with the displacement sensor for generating a velocity signal and an acceleration signal based on the displacement signal and a processing module in operative communication with the calculation module that is configured to determine an occurrence of the leading edge of the tool passing from the first medium to the second medium based only on the displacement signal, the velocity signal and the acceleration signal. A drawback of this known surgical power drill is that the reference data used to determine the transition of the leading edge of the tool from a first medium to a second medium include only punctual threshold values for the displacement, velocity and acceleration of the tool solely at the instant of the transition of the tool from the first medium to the second medium.

BRIEF SUMMARY OF THE INVENTION

It is an object of the invention to provide a surgical cutting or drilling device with means to determine a transition of the cutting tool or drill bit from a first medium having a first density to a second medium having a different second density during a cutting or drilling process which includes a numerical procedure of a significantly higher robustness using displacement characteristics only.

The invention solves the posed problem with a surgical instrument comprising the features of claim 1 and with a method for bone screw length estimation from drilling characteristics comprising the features of claim 55.

The advantages of the surgical instrument can essentially be seen therein that:
- the determination of a transition of the cutting tool or drill bit is based on a plurality of reference graphs of the distance covered by the cutting tool or drill bit wherein each reference graph extends within a time window including a first time period before the reference point of the transition and a second time period after the reference point of the transition so that in the case of a surgical drilling device the significance of the detection of the point where the drill bit exits the cortex of a bone can be improved;
- the processing unit can report two values for the position of the transition of the drill bit from a first medium to a second medium which occur at the positions where the cutting tip of the drill bit exits the near cortex, respectively the far cortex of a bone. The surgeon can then decide whether unicortical or bicortical bone screws are to be applied; and
- due to the use of a sole position sensor the measuring unit has a simple configuration and can hence be configured as a separate unit which can be temporarily attached to a standard surgical cutting or drilling device.

Further advantageous embodiments of the invention can be commented as follows:

In a special embodiment the digital data storage further stores a predefined threshold value for the similarity measure and wherein the processing unit is programmed to trigger a transition event and report the position x of transition if the threshold value for similarity is reached.

In a further embodiment the digital data storage is configured as a buffer to hold an actual time window of the current graph G of the distance [x(t)] at least as large as the window of the reference graph $G_{Ref}$.

In a further embodiment multiple reference graphs $G_{Ref}$ are stored in the digital data storage, representing various drilling or cutting characteristics and the processing unit is suitably programmed to repeat the step of quantifying the agreement between the recorded graph G or the at least one portion of the recorded graph G to the reference graphs $G_{Ref}$ by means of a similarity measure for all stored reference graphs $G_{Ref}$ and finding the overall best fit between graph G and all reference graphs $G_{Ref}$ to identify the position x of transition in the recorded graph G.

In another embodiment each reference graph $G_{Ref}$ is specified by at least 10 values, preferably at least 20 values for the distance [x(t)] covered by a cutting tool or drill bit which are subsequent with respect to time within the second time period after the reference point of a transition.

In again another embodiment each reference graph $G_{Ref}$ is specified by at least 30 values, preferably at least 40 values for the distance [x(t)] covered by a cutting tool or drill bit which are subsequent with respect to time within the first time period before the reference point of a transition.

By means of using a plurality of values for the distance [x(t)] covered by a cutting tool or drill bit before and after the reference point of a transition permits the advantage of an improved robustness of the algorithm because the detection of a transition of the cutting tool or drill bit is not restricted to features at the point of transition only but is performed by characterizing the motion of the cutting tool or drill bit before and after the point of transition. By this means wrongly positive events can be filtered and dismissed.

In a further embodiment the second time period after the reference point of a transition amounts to at least 0.1 seconds, preferably to at least 0.3 seconds within each reference graph $G_{Ref}$.

In a further embodiment the first time period before the reference point of a transition amounts to at least 0.3 seconds, preferably to at least 0.4 seconds within each reference graph $G_{Ref}$.

In a further embodiment the reference data specify a reference graph $G_{Ref}$ with a monotonously increasing distance [x(t)] covered by the cutting tool or drill bit in the first time period before reaching the reference point of a transition. Once the drill bit has exited the bone and comes to rest clearly after the exit the user performs an unintended further motion and further advances the drill bit. Using one of the devices known from prior art all criteria for a transition are fulfilled so that a wrong value for the point of the transition is detected and a significantly too long bone screw is selected and positioned in the bone. Due to the requirement of a constant advance velocity v>0 of the cutting tool or drill bit such an event can be filtered and dismissed.

In again a further embodiment the surgical instrument further comprises a surgical cutting or drilling device.

In another embodiment the surgical drilling device is a surgical power drill, wherein the drive unit comprises a motor and a spindle which is drivable by the motor and has a longitudinal axis so that the reference point is definable by a surface of an implant or a bone. The program performed by the processing unit permits bone screw length estimation based on drilling characteristics only.

In another embodiment the processing unit is one of a computer with a monitor, a tablet computer, a smartphone, a smartwatch or a smartglass.

In another embodiment the processing unit comprises a wireless communication device, preferably a Bluetooth module. The derived information, i.e. the measured position x of the cutting tip of the drill bit with respect to time as well as the computed point of transition may be transmitted wirelessly to an external device such as a computer with a monitor, a tablet computer, a smartphone, a smartwatch or a smartglass.

In yet another embodiment the surgical instrument further comprises a housing.

In a further embodiment the measuring device comprises attachment means, preferably an adaptor which is releasably affixable to the housing of the surgical power drill. This configuration permits the advantage that the measuring device can be configured as a separate unit which can be temporarily attached to a standard surgical power drill.

In a further embodiment the measuring device comprises clamps to releasably affix the measuring device to the housing.

In a further embodiment the adaptor is configured as a framework attachable to the housing, preferably an annular framework to be secured to the housing by means of a press fit or via a clamp collar.

In again a further embodiment the measuring device is integral with the housing.

In another embodiment the similarity measure applied to select the portion of the graph G which best fits the reference graph $G_{Ref}$ to find the position x of transition in the recorded graph G is a pattern recognition approach, preferably a shape context descriptor.

In another embodiment the reference data specifies a statistical representation of a plurality of prospectively recorded graphs G in the range of a transition of a cutting tool or drill bit from a first medium having a first density to a second medium having a different second density during a cutting or drilling process.

In a further embodiment the reference data are continuously amended during the use of the cutting or drilling device.

In a further embodiment the amendment of the reference data is performed by machine learning algorithms, preferably by involving use of a neural network.

In another embodiment the measuring device comprises a contactless displacement sensor.

Preferably, the contactless displacement sensor is a triangulation distance sensor and comprises a light transmitter and a corresponding receiver.

In another embodiment the contactless displacement sensor comprises a LED light transmitter.

In a further embodiment the measuring device includes a laser device which comprises a laser module and one or more electronic light sensors, preferably charge-coupled devices (CCD) to perform laser triangulation for displacement assessment. The configuration of the measuring device with a use of a laser device for displacement assessment by means of triangulation permits a simple configuration of the measuring device without a mechanical arm between the displaceable member and the sensor. Thereby the work field of the surgeon is not occupied nor is the field of view obstructed. Contactless distance measurement reduces the contamination risk of the patient and does not influence the drilling process as opposed to mechanical contact measurement. Furthermore, a significantly larger measuring range is achieved, e.g. 15 cm-30 cm compared to 6.4 cm of the known devices so that a large variety of drill bits and drill sleeves with different lengths can be used.

In again a further embodiment the contactless displacement sensor is based on radar, preferably a millimeter-wave radar sensor.

In another embodiment the contactless displacement sensor is an ultrasonic distance sensor.

In a further embodiment the contactless displacement sensor comprises a reflector slideable along a drill bit and configured to abut an implant, a bone or an instrument.

In a further embodiment the processing unit additionally comprises a display or a loud speaker. The derived information may be provided on a display or speaker locally mounted to the drilling machine, wherein the main output parameters are: the current position x of the cutting tip of the drill bit which coincides with the measured distance x covered by the housing in the direction of the longitudinal axis and relative to the surface of the implant, the instrument or the bone; the current velocity of the forward moving drill bit; and the position of the cutting tip of the drill bit at the transition of the drill bit from a first medium to second medium, wherefrom the suitable implant length can be derived.

In another embodiment the measuring device comprises a casing to enclose the processing unit.

Preferably, the casing enclosing the processing unit is sterilizable.

In another embodiment the measuring device comprises: a first member, which is in a fixed position relative to the housing; and a longitudinal second member, which is displaceable essentially in the direction of the longitudinal axis of the spindle relative to the first member and which comprises a front end suitable to abut a surface of a bone or an implant.

In yet another embodiment the displaceable second member comprises a drill sleeve extending in the direction of the longitudinal axis to the front end of the second member.

In a further embodiment the first member of the measuring device and preferably the processing unit are insertable into a hollow space arranged in the housing of the surgical power drill.

In again a further embodiment the first member and preferably the processing unit are part of an electronic module which additionally comprises a power supply and/or a motor for driving the surgical power drill and wherein the power supply is configured to supply the first member and preferably the processing unit and the motor with electric energy.

In another embodiment the hollow space is arranged in a handle of the housing and configured to receive the electronic module.

In another embodiment the housing comprises a top part including a sterilizable window for covering the display.

Preferably, the top part is integral with the housing and forms a casing for the display.

In a further embodiment the housing comprises at least one sterile window to provide a window for the signal emitted by the contactless displacement sensor and a reflected signal receivable by the contactless displacement sensor.

In a further embodiment the sterile window is configured as a recessed window. Critical transparent surfaces are protected against mechanical impacts and scratching during sterilization and handling to avoid compromising the light beam inlet and outlet.

In again a further embodiment the casing is attachable to the housing by means of an adaptor and comprises a cavity configured to receive the electronic module.

In another embodiment the casing comprises a lid arranged at the rear end of the casing and Including a sterilizable rear window for covering the display.

In another embodiment the casing comprises at least one sterile front window to provide a window for the signal emitted by the contactless displacement sensor and a reflected signal receivable by the contactless displacement sensor.

In another embodiment the displaceable second member comprises a clamping portion for attachment to cylindrical structures with variable diameters.

In another embodiment the clamping portion of the displaceable second member is configured to provide a frictional fit to a drill bit. By this means the advantage can be achieved that the reflector can slide along a drill bit but will not move due to gravity or small impacts. This way the reflector is pushed against a surface of an instrument or implant without the need to accurately fit the geometry of the instrument or implant.

In a further embodiment the measuring device is positioned with respect to the housing that a beam emitted by the contactless displacement sensor is oriented at an offset angle to the longitudinal axis of the spindle. This configuration permits the advantage that the diameter of the displaceable second member can be reduced.

In a further embodiment the first member of the measuring device is positioned off-center to the longitudinal axis of the spindle. Therewith the advantage can be achieved that the laser beams (emitted and reflected) are not obstructed by the drill-bit. The view of the operator is less obstructed.

In a further embodiment the measuring device comprises at least one accelerometer. By this means the device can be operated by gestures rather than buttons. Example: taring is only possible when oriented vertical (within limits) pointing downwards. Switching back to taring mode by orienting the drill vertical pointing upwards. Sleep mode and wake-up by device movement to safe energy.

In another embodiment the measuring device additionally comprises gyroscopes and/or magnetometers. This configuration permits the advantage that the absolute orientation of the drill can be tracked to control the drilling direction.

In another embodiment the surgical instrument additionally comprises a calibration device.

In a further embodiment the processing unit is programmed to compute in real-time.

In a further embodiment the processing unit comprises a data memory to store data related to bone screw lengths, preferably including a safety margin, screw head length, tip section length and screw length increments.

In a further embodiment the processing unit is suitably programmed to control the rotational speed of the spindle of the surgical power drill or to stop the spindle when the point of a transition is detected.

In a further aspect of the invention a method for bone screw length estimation from drilling characteristics using the surgical power drill according to the invention, the method comprising the following steps: A) advancing the surgical power drill coaxially to the longitudinal axis of the spindle to drill a hole in a bone and by recording the position (x) of the cutting tip of the drill bit relative to a surface of a bone or of an implant in the drilling direction with respect to time; B) determining the distance [x(t)] covered by the drill bit relative to a surface of a bone or of an implant when the cutting tip of the drill bit exits a cortex of a bone by using the stored reference data to find the position of a transition of the drill bit from a first medium to a second medium in the recorded graph G; and C) selecting a bone screw having a length corresponding to the distance [x(t)] covered by the drill bit determined under step B) under consideration of a predefined safety margin.

In a further embodiment of the method the following steps are performed before step A):
positioning the surgical power drill relative to a bone so that the front end of the displaceable second member and the cutting tip of the drill bit abut a surface of a bone or of an object; and
if required, adding an offset value stored in the data storage to the relative position; and
storing the relative position as start point (x=0) for the measurement of the position (x) of the cutting tip of the drill bit relative to a surface of a bone in the drilling direction with respect to time.

In this case the second member comprises a drill sleeve extending in the direction of the longitudinal axis to the front end of the second member.

In a further embodiment of the method the following steps are performed before step A):
positioning the surgical power drill relative to a bone so that the front end of the displaceable second member abuts a drill sleeve inserted in the soft tissue covering a bone to be treated; and
adjusting the cutting tip of the drill bit secured in the engagement means of the surgical power drill relative to the displaceable second member so that the cutting tip of the drill bit abuts a surface of a bone; and
if required, adding an offset value stored in the data storage to the relative position; and storing the relative position as start point (x=0) for the measurement of the position (x) of the cutting tip of the drill bit relative to a surface of a bone or of an implant in the drilling direction with respect to time.

In this case a separate drill sleeve can be used.

In another embodiment of the method the following steps are performed before step A):

positioning the drill bit secured in the engagement means relative to the displaceable second member by using a calibration device so that front end of the second member contacts a surface of the calibration device and the cutting tip of the drill bit abuts a stop protruding from the surface of the calibration device;

storing the relative position as start point (x=0) for the measurement of the position (x) of the cutting tip of the drill bit relative to a surface of a bone or of an implant in the drilling direction with respect to time; and positioning the surgical power drill relative to an implant, so that the front end of the displaceable second member abuts a surface of the implant.

Preferably, the first medium penetrated by the cutting tool or drill bit of the surgical instrument is cortical or trabecular bone.

Preferably, the surgical power drill according to the invention is used for the estimation of bone screw length.

A BRIEF DESCRIPTION OF THE DRAWINGS

Several embodiments of the invention will be described in the following by way of example and with reference to the accompanying drawings in which:

FIG. 9 illustrates a schematic sectional view of an implant positioned on a bone together with a drill bit and an embodiment of the displaceable member of the device according to the invention at the start point of the drilling process;

FIG. 10 illustrates a schematic sectional view of an implant positioned on a bone together with a drill bit and an embodiment of the displaceable member of the device according to the invention at the point where the drill bit abuts on the surface of a bone;

Figure 15:
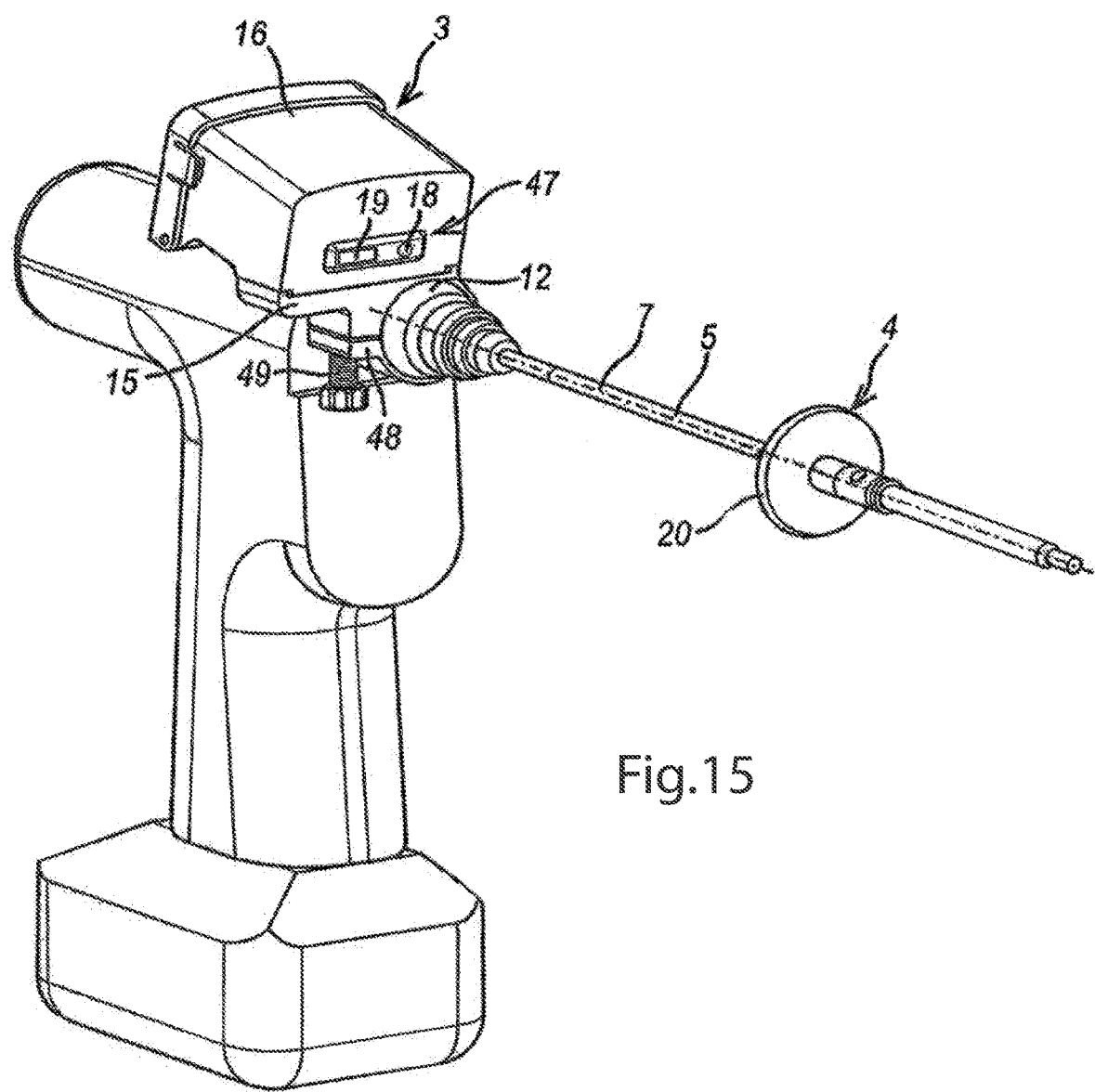
Figure 16:
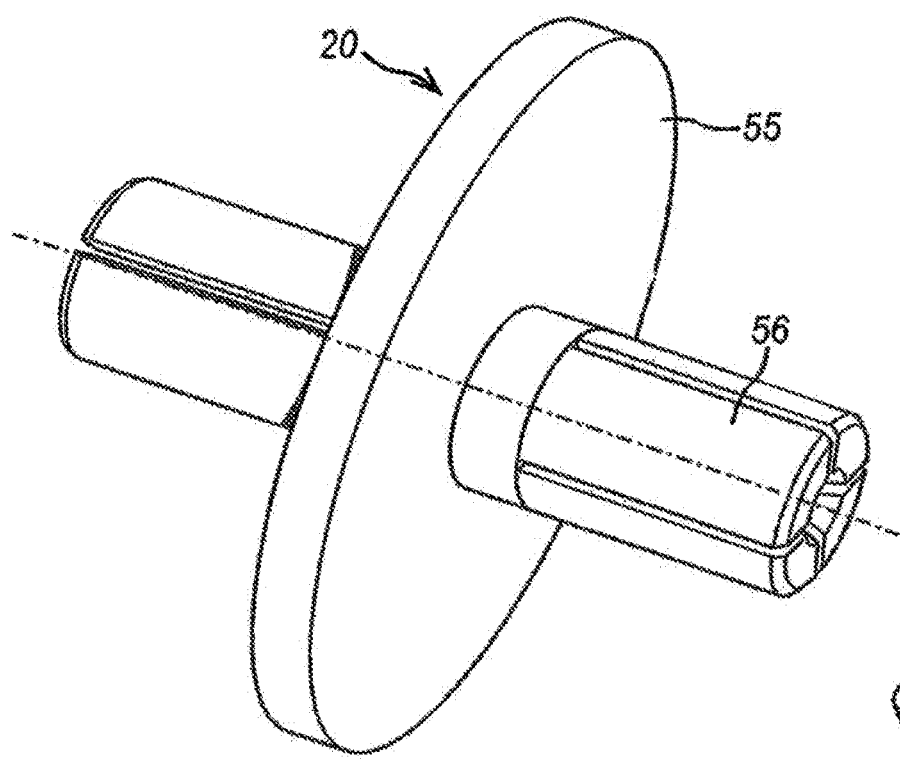
Figure 17:
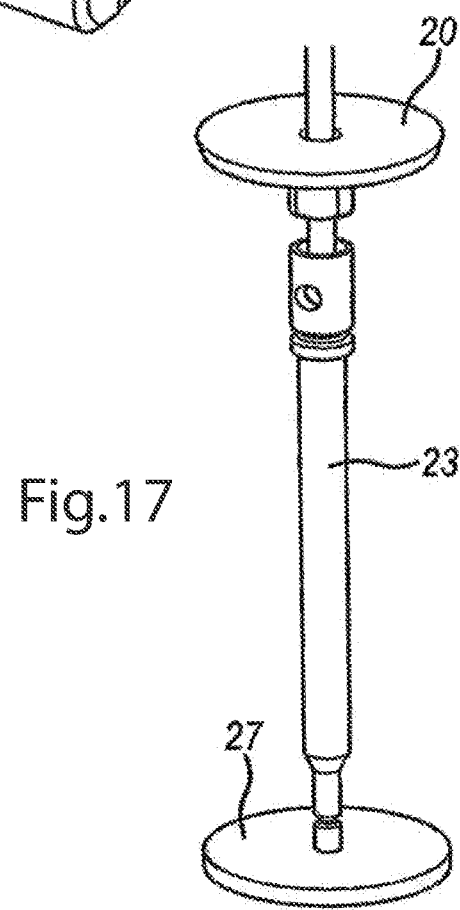

FIGS. 11*a*-11*e* illustrate perspective views of different embodiments of the displaceable second member of the device according to the invention;

FIG. 12 illustrates a perspective view of another embodiment of the device according to the invention;

FIG. 13 illustrates a perspective view of the first member of the measuring device of the embodiment of the device according to FIG. 12;

FIG. 14 illustrates another perspective view of the first member of the measuring device of the embodiment of the device according to FIG. 12;

FIG. 15 illustrates perspective view from the front of the embodiment of the device according to FIG. 12;

FIG. 16 illustrates a perspective view of a displaceable second member of the measuring device according to another embodiment of the device according to the invention; and FIG. 17 illustrates a perspective view of an assembly including the displaceable second member of the measuring device according to FIG. 16 together with a drill sleeve and a calibration device.

DETAILED DESCRIPTION OF THE INVENTION

The following description of the different embodiments of the surgical instrument 25 is—exemplarily but not limiting—directed to a surgical drilling device configured as a surgical power drill 2, wherein:

the drive unit comprises a motor and a spindle 13 which is drivable by the motor and has a longitudinal axis 7 in the direction of which the drilling path extends;

the engagement means are configured as a chuck 6 permitting to clamp a drill bit 5; and wherein the reference position is defined by a surface of an implant 26 or a bone.

The measuring device 1 can comprise a signal conditioner to convert analog signals generated by a sensor into digitized signals. Furthermore, the processing unit 14 can be provided with a timer or a clock to record the relative position x with respect to time.

Definitions

The following definition of terms and wordings currently used describe the exact meaning thereof as they are used throughout the present specification:

Position x of the cutting tip of the drill bit relative to a surface of a bone or of an implant:

During a drilling process the distance x covered by the housing 12 in the direction of the longitudinal axis 7 of the spindle 13 and relative to a surface of a bone or of an implant 26 is related with the position x of the cutting tip 9 of the drill bit 5 relative to a surface of a bone or of an implant 26 in the drilling direction because the drill bit 5 is firmly fixed in the chuck 6 of the surgical power drill 2 and positioned at the beginning of the drilling process as described in detail below.

Depending on the object into which a hole is drilled, e.g. a bone, there may be more than one point of transition 21 of the cutting tool or drill bit 5 from a first medium to a second medium, e.g. a first transition from cortical bone to cancellous bone (spongy bone) and a second transition from cortical bone to surrounding tissue. With respect to the one or more reference graphs $G_{Ref}$ the reference point of a transition is denoted with the reference numeral 21'.

Figure 1:
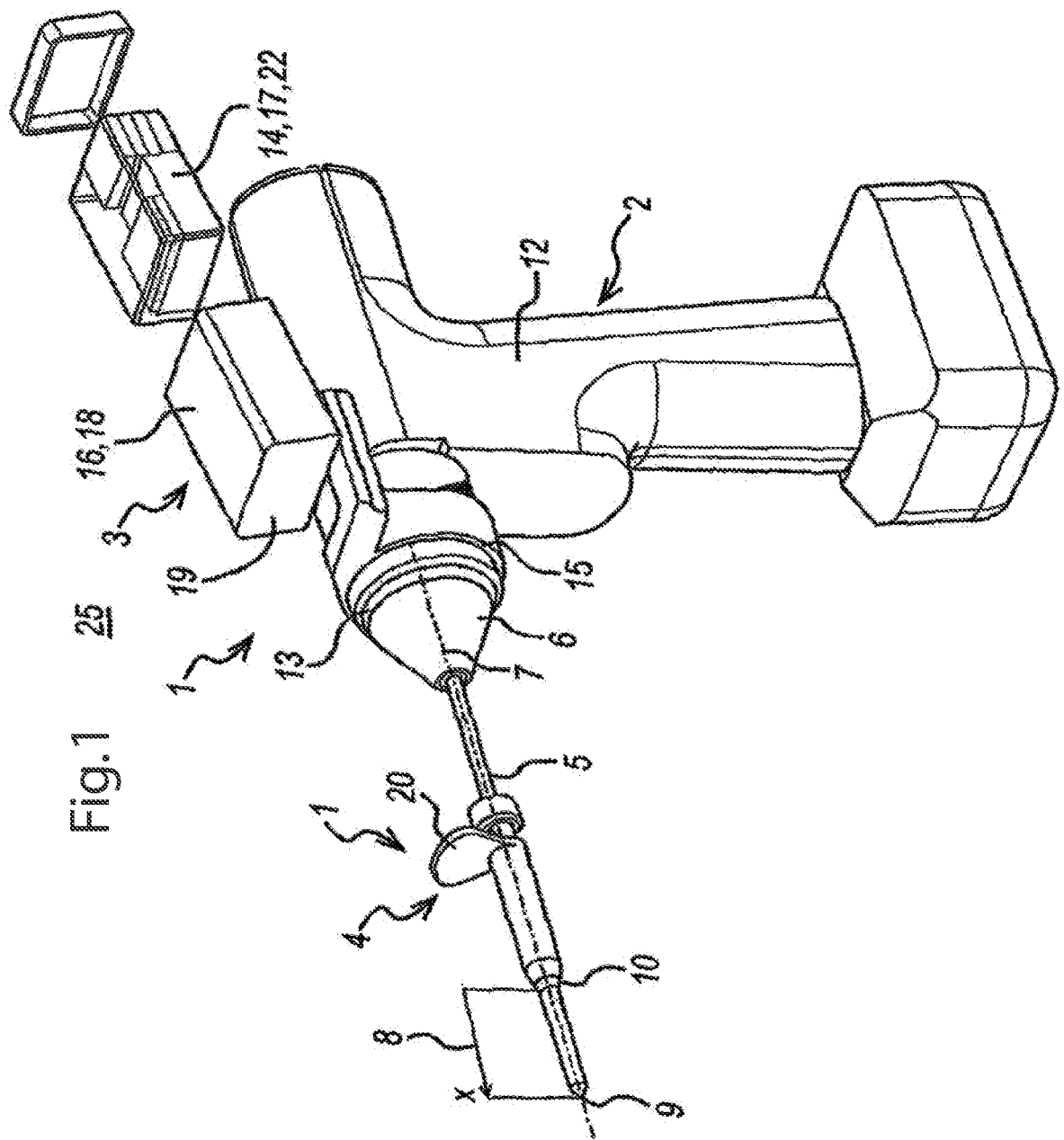
FIG. 1 illustrates a perspective view of an embodiment of the device according to the invention.

FIG. 1 illustrates an embodiment of the surgical power drill 2 according to the invention wherein the surgical power drill 2 essentially includes a housing 12 in which a motor and a spindle 13 driven by the motor are accommodated, a measuring device 1 releasably attached or fixed to the housing 12 and an adaptor 15 to secure the measuring device 1 to the housing 12. The spindle 13 has a longitudinal axis 7 and comprises a chuck 3 at a front end for clamping a drill bit 5. The measuring device 1 comprises a first member 3, which is in a fixed position relative to the housing 12 and a longitudinal second member 4, which is exemplarily but not limiting displaceable parallel or coaxial to the longitudinal axis 7 of the spindle 13 relative to the first member 3. Alternatively, the measuring device 1 can be arranged at the housing 12 so that the second member 4 is displaceable at an angle relative to the longitudinal axis 7 of the spindle 13. The systematic error which occurs due to this angulation (cosine error) can be easily compensated. This configuration has the advantage that the reflector can be smaller so that the measuring tip can be arranged closer to the drill bit 5.

The displaceable second member 4 has a front end 10, wherein in use the front end 10 of the displaceable second member 4 abuts the bone surface or a surface of an implant 26, e.g. a bone plate or a drill sleeve. The drill bit 5 can be clamped in the chuck 6 and is provided with a cutting tip 9. Furthermore, the displaceable second member 4 can comprise a drill sleeve 23 extending in the direction of the longitudinal axis 7 to the front end 10 of the second member 4.

The measuring device 1 comprises a laser device for linear displacement assessment. This laser device comprises a laser module 18 with a laser light emitting means, a reflector 20 attached to a drill sleeve 23 forming the second member 4 which is slideable along the drill bit 5 and at least one electronic light sensor 19, which is, exemplarily but not limiting, configured as a charge-coupled device (CCD) to perform laser triangulation for linear displacement assessment.

In another alternative embodiment the linear displacement assessment can be performed by using ultra sound position sensors.

To incorporate screw length determination in the drilling procedure so as to eliminate the step of depth measurement after drilling the hole in the bone the configuration of the measuring device 1 is based on the fact that during drilling an acceleration peak of the drill bit 5 occurs when the cutting tip 9 of the drill bit 5 exits a bone cortex as this is an unavoidable attribute of handheld drilling. Consequently, the housing 12 of the surgical power drill 2 together with the first member 3 of the measuring device 1 is subjected to the same acceleration.

The surgical instrument 25 further comprises a processing unit 14 and a digital data storage. The processing unit 14 is electronically directly or wirelessly connected to the measuring device 1 and suitably programmed to record a graph G of the distance [x(t)] covered by the cutting tool or drill bit 5 relative to the reference position and with respect to time during a cutting or drilling process. In the digital data storage reference data are stored which include one or more data sets each specifying a reference graph $G_{Ref}$ of the distance [x(t)] covered by a cutting tool or drill bit 5 with respect to time and within a time window 11 in the range of a transition of the cutting tool or drill bit 5 from a first medium having a first density to a second medium having a different second density during a cutting or drilling process.

Figure 2:
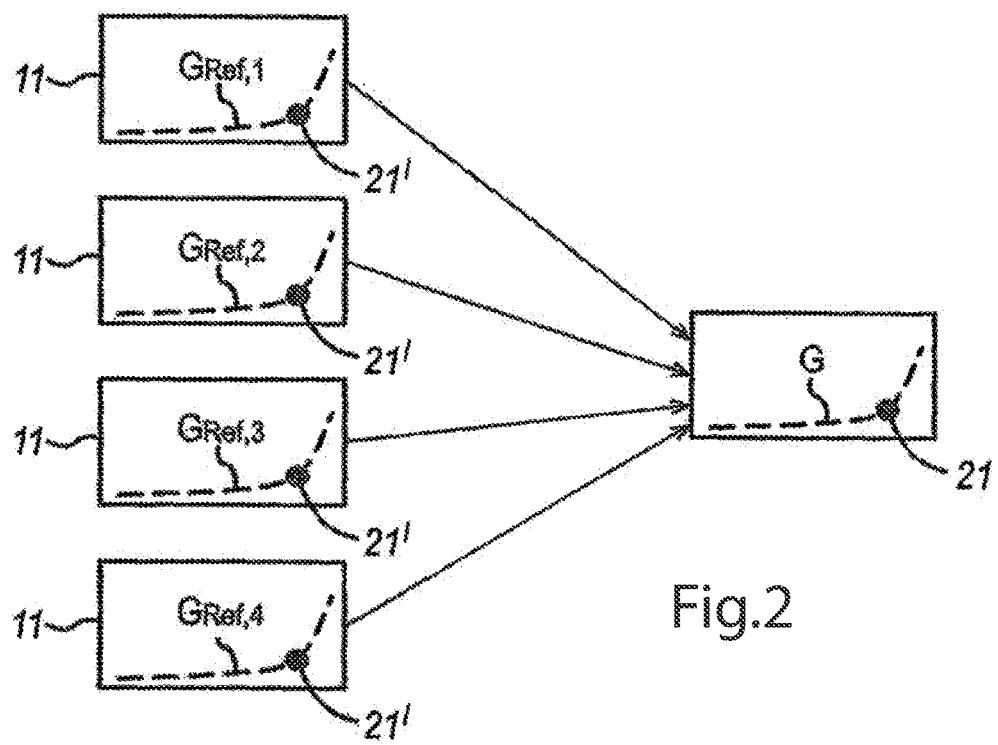
FIG. 2 illustrates a schematic representation of the reference graphs specified by the reference data and of the process performed by the processing unit.

As illustrated in FIG. 2 multiple reference graphs $G_{Ref}$ can be stored in the digital data storage, representing various drilling or cutting characteristics. The processing unit 14 is suitably programmed to repeat the step of quantifying the agreement between the recorded graph G or the at least one portion of the recorded graph G to the reference graphs $G_{Ref}$ by means of a similarity measure for all stored reference graphs $G_{Ref}$ and finding the overall best fit between graph G and all reference graphs $G_{Ref}$ to identify the position x of transition 21 in the recorded graph G.

Each of the one or more reference graphs $G_{Ref}$ defines a reference point of a transition 21' of the cutting tool or drill bit 5 from a first medium to a second medium, wherein the time window 11 includes a first time period before the reference point of a transition 21' and a second time period after the reference point of a transition 21'. The processing unit 14 is suitably programmed to compare the recorded graph G or at least one portion of the recorded graph G with the at least one reference graph $G_{Ref}$ by means of a similarity measure to quantify the agreement between the recorded graph G or at least one portion of the recorded graph G and the at least one reference graph $G_{Ref}$ to find the position of a transition 21 in the recorded graph G. In the case that at least one portion of the recorded graph G is used for the comparison the at least one portion of the recorded graph G extends at least in a period of time as specified by the time window 11. The processing unit 14 is programmed to compute in real-time. The digital data storage further stores a predefined threshold value for the similarity measure and the processing unit 14 is programmed to trigger a transition event and report the position x of transition 21 if the threshold value for similarity is reached.

Figure 3:
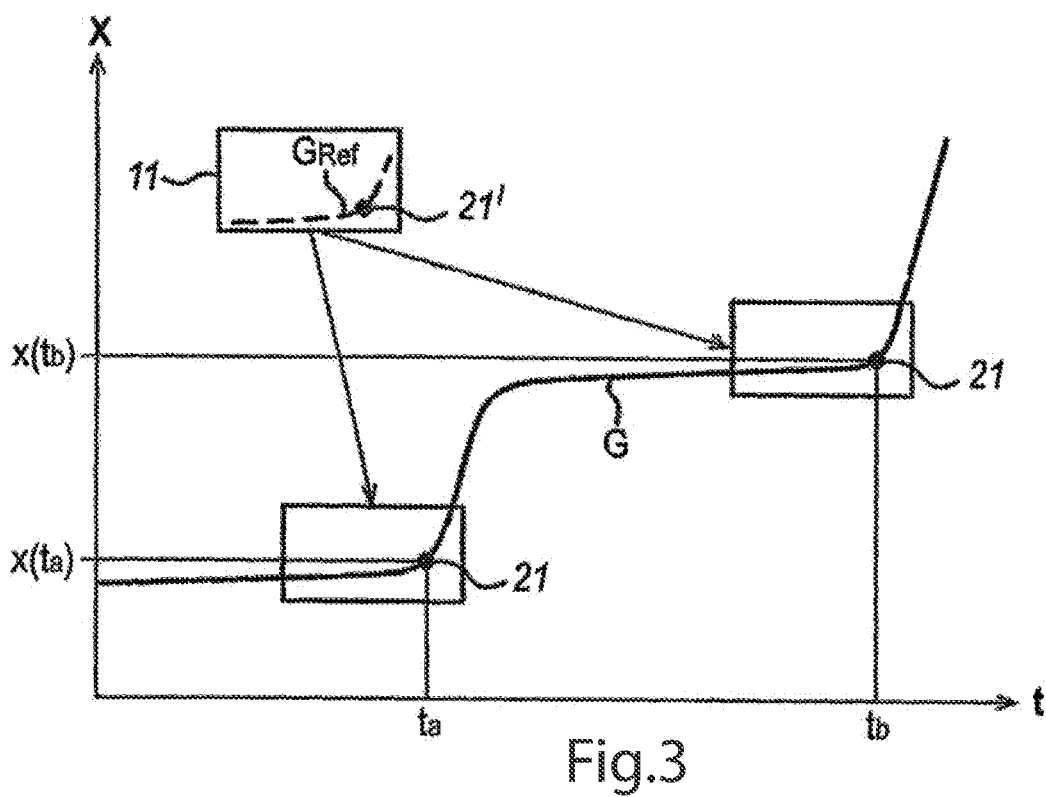
FIG. 3 illustrates a schematic representation of the process performed by the processing unit in the case of drilling a hole through a bone.

A schematic representation of the process performed by the processing unit 14 in the case of drilling a hole through a bone is illustrated in FIG. 3. The processing unit 14 can report two values for the position of a transition 21 of the drill bit 5 from a first medium to a second medium which occur at the positions where the cutting tip 9 of the drill bit 9 exits the near cortex [$x(t_a)$], respectively the far cortex [$x(t_b)$] of a bone so that the surgeon can then decide whether unicortical or bicortical bone screws are to be applied.

The digital data storage is particularly configured as a buffer to hold an actual time window of the current graph G of the distance [x(t)] at least as large as the window 11 of the reference graph $G_{Ref}$. Exemplarily but not limiting, each reference graph $G_{Ref}$ is specified by about 30 values for the distance [x(t)] covered by a cutting tool or drill bit 5 which are subsequent with respect to time within the first time period before the reference point of a transition 21' and by about 10 values for the distance [x(t)] covered by a cutting tool or drill bit 5 which are subsequent with respect to time within the second time period after the reference point of a transition 21'. Exemplarily, the first time period before the reference point of a transition 21' amounts to about 0.3 seconds and the second time period after the reference point of a transition 21' amounts to about 0.3 seconds. Additionally, the reference data inherently require a positive advance velocity v>0 of the cutting tool or drill bit 5 in the first time period before reaching the reference point of a transition 21'. The similarity measure applied to select the portion of the graph G which best fits the reference graph $G_{Ref}$ to find the position x of transition 21 in the recorded graph G can be a pattern recognition approach, exemplarily but not limiting a shape context descriptor. The reference data specifies a statistical representation of a plurality of prospectively recorded graphs G in the range of a transition of a cutting tool or drill bit 5 from a first medium having a first density to a second medium having a different second density during a cutting or drilling process. Furthermore, the reference data are continuously amended according to the use of the cutting or drilling device, wherein the amendment of the reference data can be performed by machine learning algorithms, preferably by involving use of a neural network.

The measuring device 1 particularly measures and records the relative motion between the displaceable second member 4 and the first member 3 which is fixed with respect to the housing 12. Since the drill bit 5 is firmly clamped in the chuck 6 the relative motion between the displaceable second member 4 and the first member 3 coincides with the relative motion of the cutting tip 9 of the drill bit 5 with respect to the front end 10 of the displaceable second member 4. Therefore, the measuring device 1 measures and records the relative motion of the drill bit 5 in the drilling direction in real time with respect to the bone surface or to the surface of an implant on which the front end 10 of the displaceable second member 4 of the measuring device 1 abuts. The motion of the drill bit 5 relative to the displaceable second member 4 of the measuring device 1 is a one-dimensional translational motion and the position x of the cutting tip 9 of the drill bit 5 relative to the front end 10 of the displaceable second member 4 at any moment is given by the x coordinate of the cutting tip 9 along the x-axis 8 which in this case forms the reference frame. The position x or x coordinate of the cutting tip 9 is set to 0 at the beginning of the drilling procedure, e.g. when the cutting tip 9 of the drill bit 5 is flush with the front end 10 of the displaceable second member 4.

For this purpose the position x or x coordinate of the cutting tip 9 of the drill bit 5 with respect to time is recorded by the processing unit 14 which is integrated in the first member 3 of the measuring device 1.

Exemplarily, but not limiting, the processing unit 14 is configured as a digital processing unit and comprises a microprocessor having a processor register to record the position of the second member 4 relative to the first member 3. As described above the position of the second member 4 relative to the first member 3 coincides with the position x or x coordinate of the cutting tip 9 of the drill bit 5 relative to the front end 10 of the displaceable second member 4.

The drill distance to the exit from the second cortex, i.e. the position x or x coordinate of the cutting tip 9 of the drill bit 5 when the cutting tip 9 exits the far cortex is automatically computed based on the process performed by the processing unit 14. Based on this position x or x coordinate the required screw length, preferably including a safety margin can be estimated. For this purpose the processing unit 14 can comprise a data memory to store data related to bone screw lengths, preferably including safety margin, screw head length, tip section length and screw length increments.

The measuring device 1 and particularly the displacement sensors can be either integrated in the housing 12 or can be temporarily attachable thereto. In a temporarily attachable configuration the measuring device 1 comprises attachment means in the form of an adaptor 15 which is releasably affixable to the housing 12 of the surgical power drill 2. This adaptor 15 is exemplarily but not limiting configured as an annular framework attachable to the housing 12 by means of a press fit or via a clamp collar. Alternatively, the measuring device 1 can comprise clamps to releasably affix the measuring device 1 to the housing 12.

The measuring device 1 can comprise a wireless communication device, exemplarily configured as a Bluetooth module with signal conditioner. Via the wireless communication device the data may be transmitted wirelessly to an external computer with monitor, a tablet computer, a smartphone, a smartwatch or a smart glass to compute or indicate the derived information, i.e. the measured position of the cutting tip of the drill bit with respect to time, the computed velocity with respect to time and the computed point of transition may be transmitted wirelessly to an external device such as a computer with monitor, a tablet computer, a smartphone, a smartwatch or a smartglass. Alternatively, the derived data may be provided on a display or speaker locally mounted to the surgical power drill 2.

Additionally, the measuring device 1 comprises a sterilizable casing 16 to enclose the processing unit 14, the wireless communication device and the power supply 22 for the measuring device 1, wherein the power supply 22 includes one or more rechargeable or non-rechargeable batteries arrangeable in the casing 16.

Figure 7:
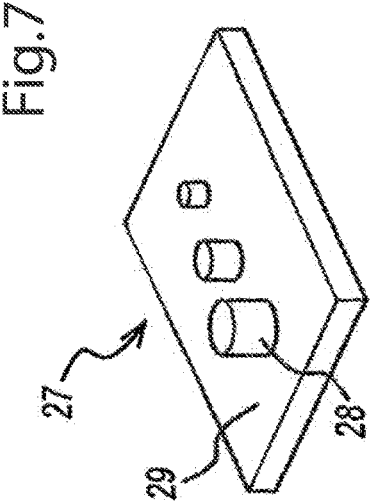
FIG. 7 illustrates a perspective view of a calibration device for use with the device according to the invention.
Figure 8:
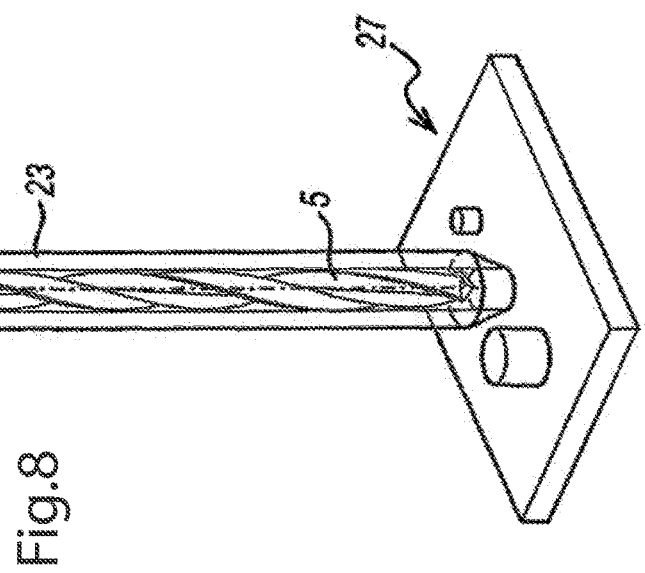
FIG. 8 illustrates a perspective view of the calibration device of FIG. 7 together with a drill bit and an embodiment of the displaceable second member of the device according to the invention.
Figure 11A:
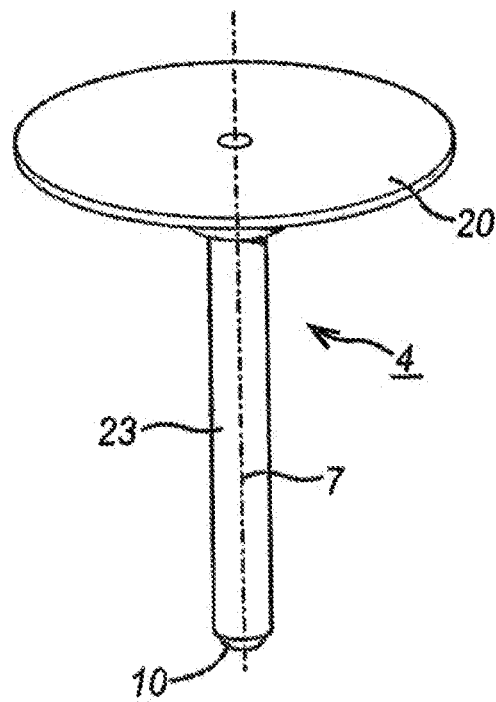
Figure 11B:
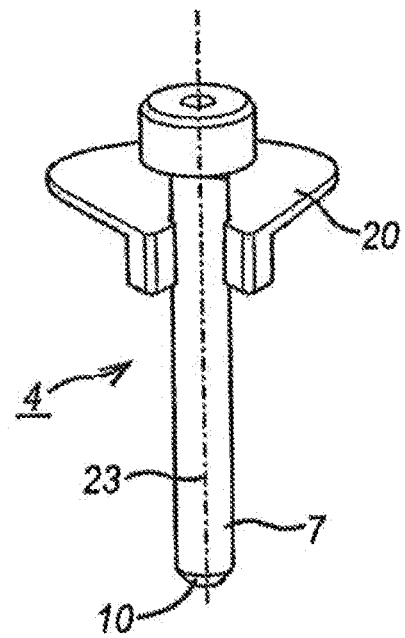
Figure 11C:
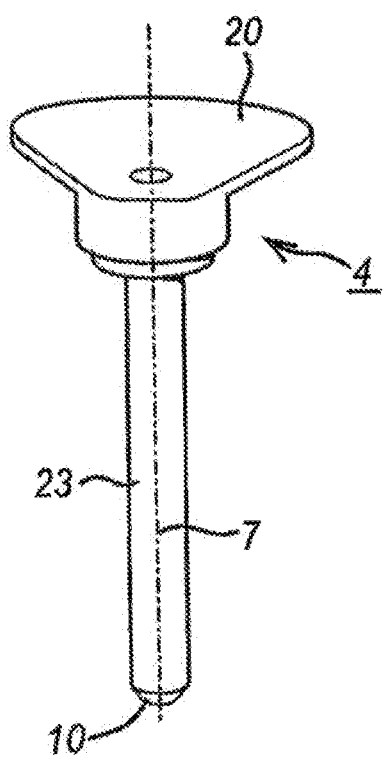
Figure 11D:
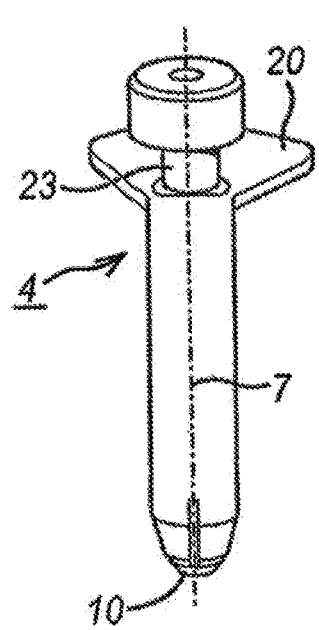
Figure 11E:
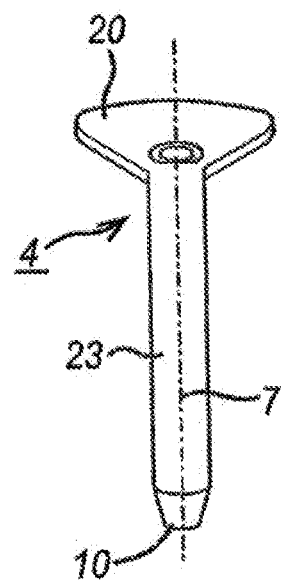

Furthermore, the device 25 can additionally comprise a calibration device 27 as illustrated in FIGS. 7 and 8 and described in more detail below.

Figure 4:
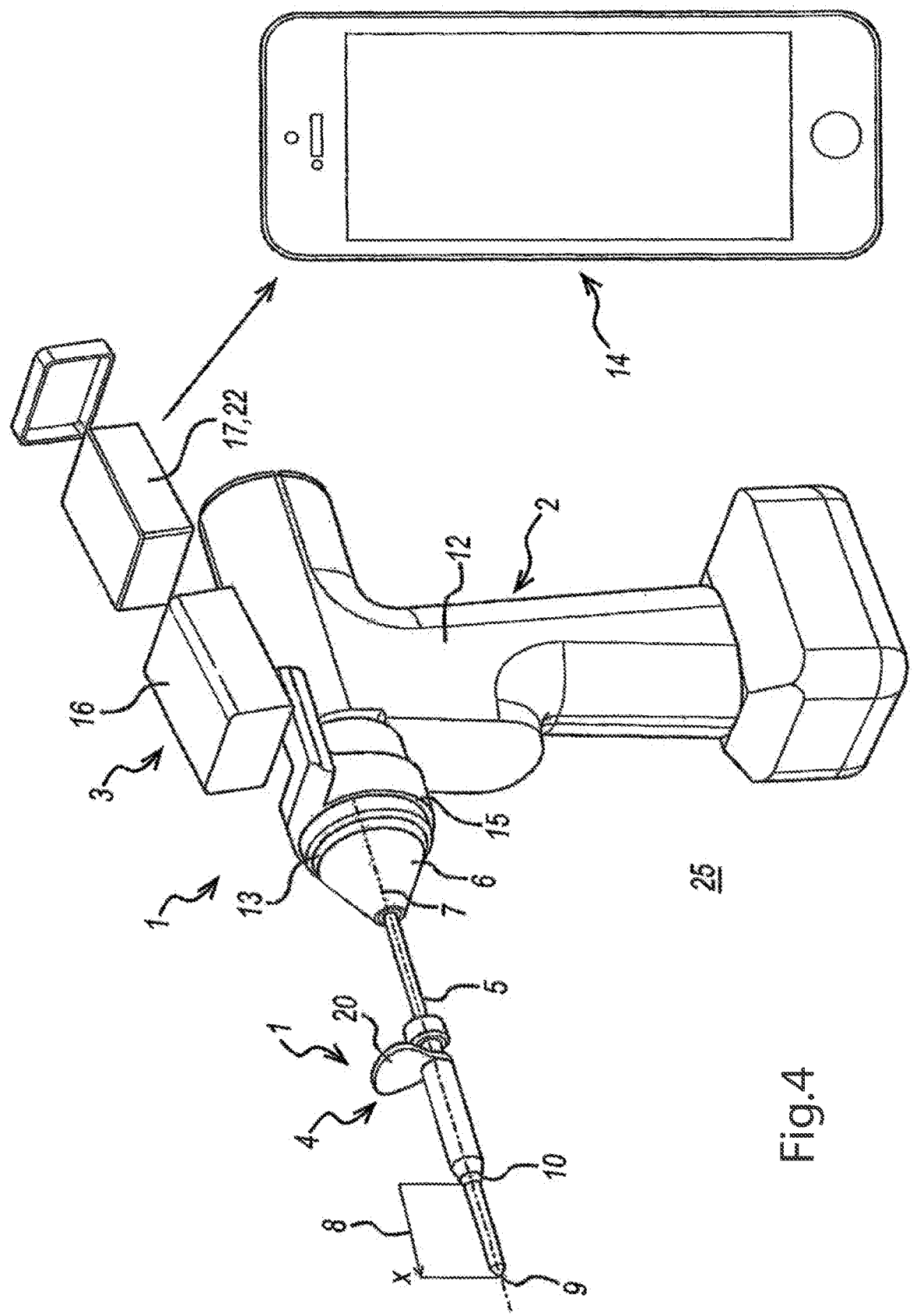
FIG. 4 illustrates a perspective view of another embodiment of the device according to the invention.

Another embodiment of the device 25 according to the invention is illustrated in FIG. 4, wherein the device 25 of FIG. 2 differs from the embodiment of FIG. 1 only therein that the processing unit 14 is an external unit, e.g. a computer with monitor, a tablet computer, a smartphone, a smartwatch or a smartglass, and that the measuring device 1 comprises a wireless data transmission device 17 and the processing unit 14 includes a wireless data receiving device so that the measured distance x covered by the housing 12 in the direction of the longitudinal axis 7 and relative to a surface of an implant 26 or a bone can be transmitted from the measuring device 1 to the external processing unit 14 and recorded with respect to time. The external processing unit 14 can comprise a microprocessor similar to the embodiment of FIG. 1 or can comprise a central processing unit.

Figure 5:
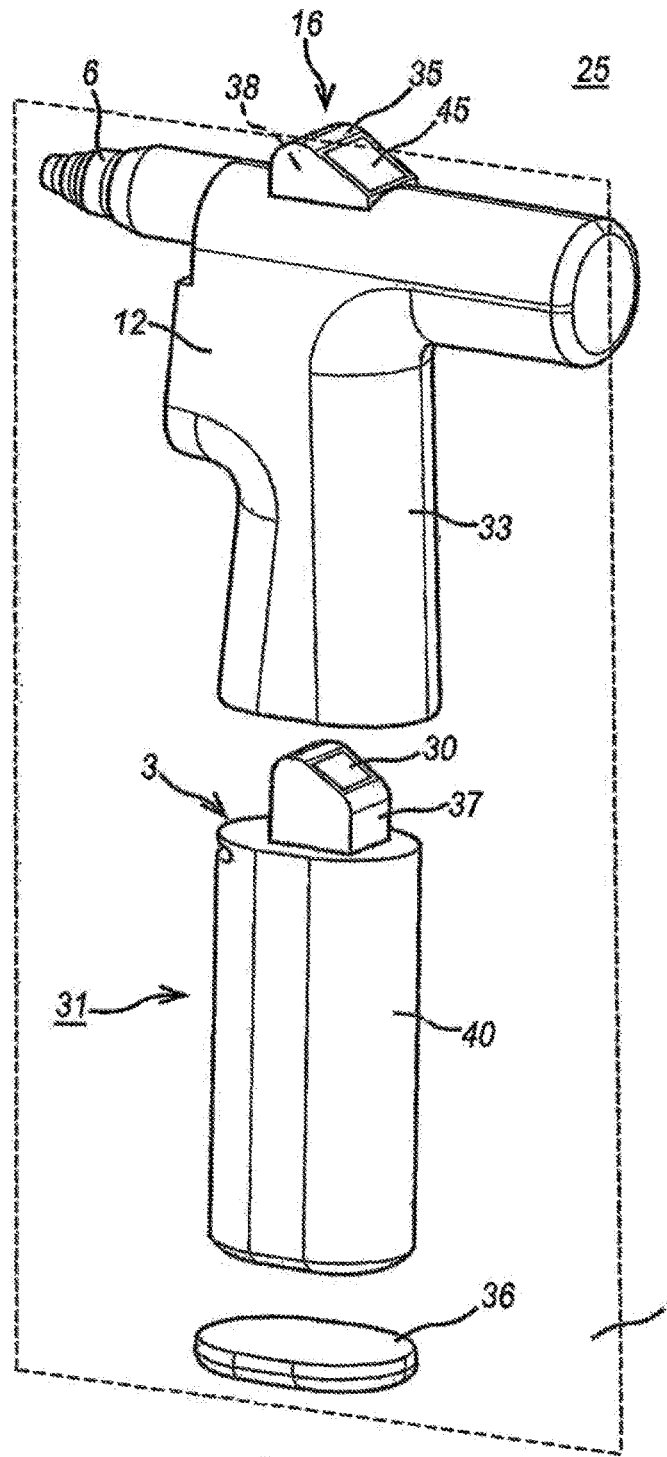
FIG. 5 illustrates a perspective view of a further embodiment of the device according to the invention.
Figure 6:
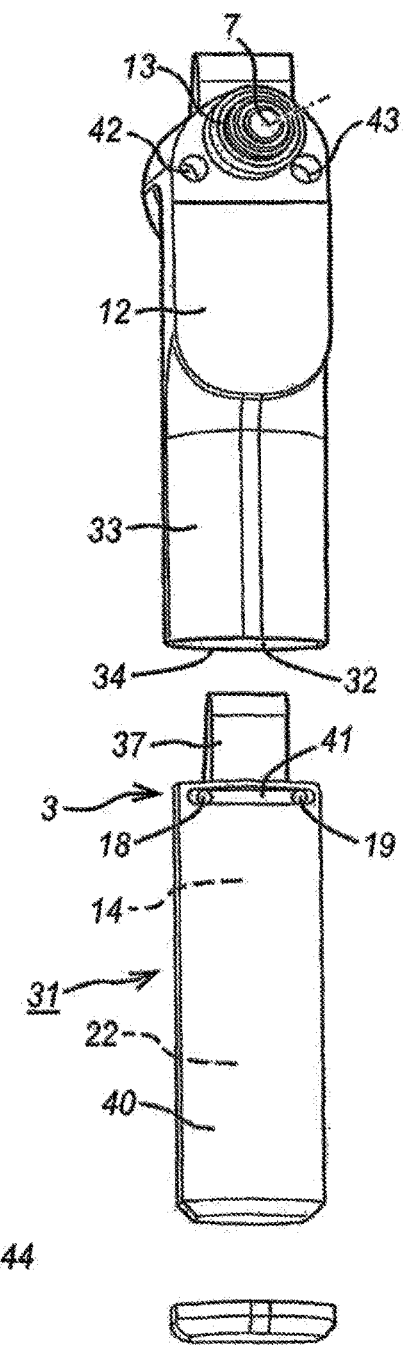
FIG. 6 illustrates an exploded front view of the embodiment of FIG. 5.

A further embodiment of the device 25 according to the invention is illustrated in FIGS. 5 and 6, wherein the measuring device 1 of the embodiment of FIGS. 5 and 6 differs from the embodiment of FIG. 1 therein that the first member 3 including the laser module 18 for emitting a laser beam and the receiver for triangulation, e.g. an electronic light sensor 19 in the form of a photodiode or a charge-coupled device (CCD) is configured as a part of an electronic module 31. This electronic module 31 is insertable into a hollow space 32 formed in the handle 33 of the housing 12, wherein the hollow space 32 extends from an opening 34 at the bottom of the handle 33 to the top part 35 of the housing 12. The opening 34 can be closed by means of a cover 36 which is attachable to the bottom of the handle 33.

Apart from the first member 3 the electronic module 31 comprises a display 30 which is arranged in an upper part 37 of the electronic module 31, wherein this upper part 37 is shaped and dimensioned to fit into a respective cavity 38 configured in the top part 35 of the housing 12. Furthermore, the electronic module 31 has a lower part 40 including the laser module 18, the electronic light sensor 19, the processing unit 14 and a power supply 22 for driving the surgical power drill 2 and for supplying the laser module 18, the light sensor 19 and the processing unit 14. Exemplarily, the power supply 22 can be a battery or an accumulator. The lower part 40 of the electronic module 31 is shaped and dimensioned to fit into the hollow space 32 in the handle 33 of the housing 12. A laser window 41 is arranged at the front of the lower part 40 and just below the upper part 37 of the electronic module 31 so as to match the laser beam and the electronic light sensor 19 with respective windows 42, 43 (FIG. 6) in the housing 12.

A first and a second sterile window 42, 43 are arranged in the housing 12 of the surgical power drill 2 to provide windows for the laser beam emitted by the laser module 18 and the reflected beam received by the electronic light sensor 19. The first and second sterile windows 42, 43 are arranged in the front of the housing 12 and—when viewed in a front view—below the longitudinal axis 7 of the spindle 13 and located on opposite sides of a middle plane 44 of the surgical power drill 2 which contains the longitudinal axis 7 and at a distance from the middle plane 44 which permits the laser beam and the reflected beam to pass beside the spindle 13 and the chuck 6 of the surgical power drill 2.

The top part 35 of the housing 12 forms a casing 16 for the display 30, wherein the casing 16 is, exemplarily but not limiting, integral with the housing 12 of the surgical power drill 2 and encompasses the cavity 38. This casing 16 comprises a third sterile window 45 for covering the display 30. Further the casing 16 is arranged at the housing 12 opposite the handle 33 of the surgical power drill 2. The third sterile window 45 is angled relative to a plane orthogonal to the longitudinal axis 7 of the spindle 13 and directed towards the rear end of the housing 12.

Exemplarily but not limiting the measuring device 1 is suitably configured to control the rotational speed of the spindle 13 of the surgical power drill 2 so that the power supplied to the electric motor of the power drill 2 can be shut down when a peak is detected by means of the measuring device 1 to thereby prevent plunging of the drill bit 5.

Again another embodiment of the device 25 according to the invention is illustrated in FIGS. 12-15, wherein the measuring device 1 of the embodiment of FIGS. 12-15 differs from the embodiment of FIG. 1 therein that the first member 3 includes an electronic module 31 which comprises apart from the laser module 18 for emitting a laser beam and the receiver for triangulation, e.g. an electronic light sensor 19 in the form of a photodiode or a charge-coupled device (CCD) a display 30. Further the electronic module 31 comprises the processing unit 14 and the power supply 22 for the measuring device 1. The display 30 is arranged at the rear side 46 of the electronic module 31. Similarly to the embodiment of FIG. 1 the sterilizable casing 16 is attachable to the surgical power drill 2 and comprises a cavity 38 to receive the electronic module 31. A sterile front window 47 is arranged in the front of the casing 16 to let through the laser beam emitted by the laser module 18 and the reflected beam reflected by means of the reflector 20 arranged at the second member 4 of the measuring device 1.

The laser module 18 and the electronic light sensor 19 which receives the reflected beam to perform the triangulation are arranged laterally spaced from each other in the electronic module 31 so that—when viewed in a front view of the assembled first member 3—the laser beam and the reflected beam pass above the longitudinal axis 7 of the spindle 13.

The casing 16 comprises an adaptor 15 to secure the first member 3 of the measuring device 1 to the housing 12, wherein the adaptor 15 is releasably affixable to the housing 12 of the surgical power drill 2. This adaptor 15 is, exemplarily but not limiting, configured as an annular framework attachable to the housing 12 by means of a clamp collar 48 that is fixable, e.g. to the stationary part of the spindle 13 by means of a clamping screw 49.

The clamp collar 48 is positioned at the casing 16 laterally offset with respect to a longitudinal central plane of the casing 16 to permit the laser beam and the reflected beam to pass beside the drill bit 5. Furthermore, by means of the adaptor 15 the casing 16 is attached to the surgical power drill 2 at an angle with respect to the longitudinal axis 7 so that the laser beam is emitted at an angle to the longitudinal axis 7 permitting a reduced size of the reflector 20 of the second member 4 of the measuring device 1.

The casing 16 is sterilizable and configured as a separate piece arranged on top of the housing 10. The cavity 38 has an opening at the rear side of the casing 16 and can be closed by means of a lid 51 which is rotatable about an axis located at the lower side of the casing 16 and extending orthogonally to the longitudinal axis. The lid 51 comprises a sterile rear window 52 for covering the display 30, wherein—when the lid 51 is closed —the rear window 52 is angled relative to a plane orthogonal to the longitudinal axis 7 of the spindle 13 and directed towards the rear end of the housing 12.

Exemplarily but not limiting, an actuator 53 for a power switch of the electronic module 31 can be arranged at the inside of the lid 51 so that when the lid 51 is closed energy is supplied from the power supply 22 to the electronic components of the measuring device 1. To operate the processing unit 14, the laser module 18 and the electronic light sensor 19 one or more buttons 54 can be positioned at the rear side of the electronic module 31. The sterile rear window 52 can be provided with recesses so as to provide weakened areas in the rear window 52 which permit to actuate the one or more buttons 54 when the lid 51 is in its closed position.

The processing unit 14 of the embodiments of FIGS. 1, 4-6 and 12-15 comprises a microprocessor or a central processing unit which includes a processor register to record the distance x covered by the housing 12 in the direction of the longitudinal axis 7 and relative to a surface of an implant 26 or a bone with respect to time during a drilling process.

It has to be noted that real-time feedback of current drill depth alone can be of high value for the surgeon. Further valuable information is delivered by the current drilling speed. This helps the surgeon to control his feed rate to avoid mechanical or heat damage of the bone or it can be used to estimate the bone quality.

FIG. 16 illustrates another embodiment of the reflector 20 which is not integral with or attached to a drill sleeve 23. The reflector 20 is clampable onto the drill bit 5 in such a way that it can slide on the drill bit 5 so that the reflector 20 is independent from the configuration of the drill sleeve 23. The reflector 20 has a disc shaped portion 55 and on each side adjoining thereto a clamping portion 56 comprising longitudinal slots so as to form tongues suitable to exert radial pressure onto the drill bit 5.

The method for bone screw length estimation from drilling characteristics essentially comprises the steps: A) advancing the surgical power drill 2 coaxially to the longitudinal axis of the spindle 13 to drill a hole in a bone and by recording the position (x) of the cutting tip 9 of the drill bit 5 relative to a surface of a bone or of an implant 26 in the drilling direction with respect to time; B) determining the instant when the cutting tip 9 of the drill bit 5 exits a cortex of a bone by using the selected reference graph $G_{Ref}$ and the reference position of the transition 21' of the drill bit 5 from a first medium to a second medium defined by the selected reference graph $G_{Ref}$; C) determining the distance [x(t)] covered by the drill bit 5 at the instant determined under step B); and D) selecting a bone screw having a length corresponding to the distance [x(t)] covered by the drill bit 5 determined under step C) under consideration of a predefined safety margin.

As described above the position x of the cutting tip 9 of the drill bit 5 relative to a surface of a bone or of an implant 26 in the drilling direction is set to zero at the beginning of the drilling process. However, this zero position of the cutting tip 9 of the drill bit 5 depends on the fact whether:
1) the displaceable second member 4 comprises a drill sleeve 23 extending in the direction of the longitudinal axis 7 to the front end 10 of the second member 4 as illustrated in FIGS. 3, 4 and 11a-11e; or whether 2) the drill sleeve is a separate member previously inserted in the soft tissue covering the bone to be treated; or whether 3) the zero position of the cutting tip 9 is to be set with respect to an implant 26, e.g. a bone plate. In case the drill bit 5 is guided in a drill sleeve 23 which during drilling contacts or attaches to a bone plate and hence doesn't allow the cutting tip 9 of the drill bit 5 to abut the upper surface of the bone plate (FIG. 9) a calibration device 27 providing a physical stop 28 inside the drill sleeve 23 at a height corresponding with the upper surface of the bone plate can be used to determine the start point of the measurement (FIG. 8). Alternatively, if the lengths of drill bit 5 and drill sleeve 23 are known, the start point can be computed from this data.

In the case of the above variant 1) the method comprises before step A) the following steps:
positioning the surgical power drill 2 relative to a bone so that the front end 10 of the displaceable second member 4 and the cutting tip 9 of the drill bit 5 abut a surface of a bone; and
storing the relative position as start point (x=0) for the measurement of the position x of the cutting tip 9 of the drill bit 5 relative to a surface of a bone in the drilling direction with respect to time.

In the case of the above variant 2) the method comprises before step A) the following steps:
positioning the surgical power drill 2 relative to a bone so that the front end 10 of the displaceable second member 4 abuts a drill sleeve 23 inserted in the soft tissue covering a bone to be treated; and
adjusting the cutting tip 9 of the drill bit 5 secured in the chuck 6 of the surgical power drill 2 relative to the displaceable second member 4 so that the cutting tip 9 of the drill bit 5 abuts a surface of a bone; and
storing the relative position as start point (x=0) for the measurement of the position x of the cutting tip 9 of the drill bit 5 relative to a surface of a bone in the drilling direction with respect to time.

In the case of the above variant 3) the method comprises before step A) the following steps (FIGS. 9 and 10):
positioning the drill bit 5 secured in the chuck 6 relative to the displaceable second member 4 by using a calibration device 27 (FIGS. 7 and 8) so that front end 10 of the second member 4 contacts a surface 29 of the calibration device 27 and the cutting tip 9 of the drill bit 5 abuts a stop 28 protruding from the surface 29 of the calibration device 27;
storing the relative position as start point (x=0) for the measurement of the position x of the cutting tip 9 of the drill bit 5 relative to a surface of a bone or of an implant 26 in the drilling direction with respect to time; and
positioning the surgical power drill 2 relative to an implant 26, e.g. a bone plate, so that the front end 10 of the displaceable second member 4 abuts a surface of the implant 26 (FIG. 9).

FIG. 17 illustrates a further embodiment of the calibration device 27. The reflector 20 as well as the calibration device 27, e.g. illustrated in FIGS. 7 and 8 can be made for single use. In other embodiments the drill sleeve 23 according to one of the embodiments illustrated in FIGS. 11*a*-11*e*, 16 and 17 can be configured as a disposable member as well and can for this purpose be connected to the calibration device 27 via a predetermined breaking point.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

The invention claimed is:

1. A surgical instrument, comprising:
a drive unit;
a cutting tool or drill bit engageable with the drive unit;
a measuring device attached to or integral with the surgical instrument, wherein the measuring device (1) is configured to measure a distance covered by the cutting tool or drill bit along a cutting or drilling path with respect to time and relative to a reference position;
a processing unit electronically directly or wirelessly connected to the measuring device and suitably programmed to record a graph of the distance covered by the cutting tool or drill bit relative to the reference position and with respect to time during a cutting or drilling process; and
a digital data storage,
characterized in that
in the digital data storage, reference data are stored which include at least one data set specifying at least one reference graph of the distance covered by the cutting tool or drill bit with respect to time and within a time window in a range of a transition of the cutting tool or drill bit from a first medium having a first density to a second medium having a different second density during a cutting or drilling process, wherein
the at least one reference graph defines a reference point of the transition of the cutting tool or drill bit from a first medium to a second medium; and wherein
the time window includes a first time period before the reference point of the transition and a second time period after the reference point of the transition; and
the processing unit is suitably programmed to compare the recorded graph with the at least one reference graph by means of a similarity measure to quantify an agreement between the recorded graph or at least one portion of the recorded graph and the at least one reference graph to find a position of a transition in the recorded graph.

2. The surgical instrument according to claim 1, wherein the digital data storage further stores a predefined threshold value for the similarity measure and wherein the processing unit is programmed to trigger an event and report the position of the transition if the threshold value for similarity is reached.

3. The surgical instrument according to claim 2, wherein the digital data storage is configured as a buffer to hold an actual time window of a current graph of the distance at least as large as the time window of the at least one reference graph.

4. The surgical instrument according to any one of claims 1 to 3, wherein multiple reference graphs are stored in the digital data storage, representing various drilling or cutting characteristics and wherein the processing unit is suitably programmed to repeat the step of quantifying the agreement between the recorded graph or the at least one a portion of the recorded graph to the reference graphs by means of a similarity measure for all stored reference graphs and finding an overall best fit between the recorded graph and all reference graphs to identify the position of the transition in the recorded graph.

5. The surgical instrument according to claim 1, wherein each at least one reference graph is specified by at least 10 values for the distance covered by the cutting tool or drill bit which are subsequent with respect to time within the second time period after the reference point of the transition.

6. The surgical instrument according to claim 5, wherein each at least one reference graph is specified by at least 30 values for the distance [x(t)] covered by a cutting tool or drill bit which are subsequent with respect to time within the first time period before the reference point of the transition(21').

7. The surgical instrument according to claim 1, wherein within each at least one reference graph the second time period after a point of the transition amounts to at least 0.1 seconds.

8. The surgical instrument according to claim 7, wherein within each reference graph the first time period before the reference point of the transition amounts to at least 0.3 seconds.

9. The surgical instrument according to claim 1, wherein the reference data specify the at least one reference graph with a monotonously increasing distance covered by the cutting tool or drill bit in the first time period before reaching the reference point of the transition.

10. The surgical instrument according to claim 1, wherein the surgical instrument further comprises a surgical cutting or drilling device.

11. The surgical instrument according to claim 10, wherein the surgical cutting or drilling device is a surgical power drill, wherein the drive unit comprises a motor and a spindle which is drivable by the motor and has a longitudinal axis so that the reference point is definable by a surface of an implant or a bone.

12. The surgical instrument according to claim 11, wherein the processing unit is one of a computer with a monitor, a tablet computer, a smartphone, a smartwatch or a smartglass.

13. The surgical instrument according to claim 12, wherein the processing unit comprises a wireless communication device.

14. The surgical instrument according to claim 13, wherein the surgical instrument further comprises a housing.

15. The surgical instrument according to claim 14, wherein the measuring device comprises an adaptor which is releasably affixable to the housing of the surgical power drill.

16. The surgical instrument according to claim 14 or 15, wherein the measuring device comprises clamps to releasably affix the measuring device to the housing.

17. The surgical instrument according to claim 15, wherein the adaptor is configured as a framework attachable to the housing.

18. A use of a surgical power drill according to claim 11 for estimation of bone screw length.

19. The surgical instrument according to claim 14, wherein the measuring device is integral with the housing.

20. The surgical instrument according to claim 14, wherein the measuring device comprises a contactless displacement sensor.

21. The surgical instrument according to claim 20, wherein the contactless displacement sensor is a triangulation distance sensor and comprises a light transmitter and a corresponding receiver.

22. The surgical instrument according to claim 20 or 21, wherein the contactless displacement sensor comprises a LED light transmitter.

23. The surgical instrument according to claim 22, wherein the measuring device includes a laser device which comprises a laser module and one or more electronic light sensors configured as charge-coupled devices to perform laser triangulation for displacement assessment.

24. The surgical instrument according to claim 23, wherein the contactless displacement sensor is based on radar.

25. The surgical instrument according to claim 23, wherein the contactless displacement sensor is an ultrasonic distance sensor.

26. The surgical instrument according to claim 23, wherein the processing unit additionally comprises a display or a loud speaker.

27. The surgical instrument according to claim 26, wherein the measuring device comprises a casing to enclose the processing unit.

28. The surgical instrument according to claim 27, wherein the casing enclosing the processing unit is sterilizable.

29. The surgical instrument according to claim 27, wherein the measuring device comprises:
   a first member, which is in a fixed position relative to the housing; and
   a longitudinal second member, which is displaceable essentially in a direction of the longitudinal axis of the spindle relative to the first member and which comprises a front end suitable to abut a surface of a bone or an implant.

30. The surgical instrument according to claim 29, wherein the longitudinal second member comprises a drill sleeve extending in the direction of the longitudinal axis to the front end of the longitudinal second member.

31. The surgical instrument according to claim 30, wherein the first member of the measuring device and the processing unit are insertable into a hollow space arranged in the housing of the surgical power drill.

32. The surgical instrument according to claim 31, wherein the first member and the processing unit are part of an electronic module which additionally comprises a power supply and/or a motor for driving the surgical power drill and wherein the power supply is configured to supply the first member and the processing unit and the motor with electric energy.

33. The surgical instrument according to claim 32, wherein the hollow space is arranged in a handle of the housing and configured to receive the electronic module.

34. The surgical instrument according to claim 32, wherein the housing comprises at least one sterile window to provide a window for a signal emitted by the contactless displacement sensor and a reflected signal receivable by the contactless displacement sensor.

35. The surgical instrument according to claim 34, wherein the sterile window is configured as a recessed window.

36. The surgical instrument according to claim 35, wherein the casing is attachable to the housing by means of an adaptor and comprises a cavity configured to receive the electronic module.

37. The surgical instrument according to claim 36, wherein the casing comprises a lid arranged at a rear end of the casing and including a sterilizable rear window for covering the display.

38. The surgical instrument according to claim 37, wherein the casing comprises at least one sterile front window to provide a window for the signal emitted by the contactless displacement sensor and a reflected signal receivable by the contactless displacement sensor.

39. The surgical instrument according claim 29, wherein the longitudinal second member comprises a clamping portion for attachment to cylindrical structures with variable diameters.

40. The surgical instrument according to claim 39, wherein the clamping portion of the longitudinal second member is configured to provide a frictional fit to a drill bit.

41. The surgical instrument according to claim 29, wherein the measuring device is positioned with respect to the housing so that a beam emitted by the contactless displacement sensor is oriented at an offset angle to the longitudinal axis of the spindle.

42. The surgical instrument according to claim 29, wherein the first member of the measuring device is positioned off-center to the longitudinal axis of the spindle.

43. The surgical instrument according to claim 23, wherein the processing unit is suitably programmed to control a rotational speed of the spindle of the surgical power drill or to stop the spindle when a point of a transition is detected.

44. A method for bone screw length estimation from drilling characteristics using the surgical power drill according to claim 29, comprising the following steps:
advancing the surgical power drill coaxially to the longitudinal axis of the spindle to drill a hole in a bone and by recording a position of a cutting tip of the drill bit relative to a surface of a bone or of an implant in a drilling direction with respect to time;
determining the distance covered by the drill bit relative to a surface of a bone or of an implant when the cutting tip of the drill bit exits a cortex of a bone by using the stored reference data to find the position of the transition of the drill bit from a first medium to a second medium in the recorded graph;
selecting a bone screw having a length corresponding to the distance covered by the drill bit determined during the determining step under consideration of a predefined safety margin.

45. The method according to claim 44, wherein before the advancing step the following steps are performed:
positioning the surgical power drill relative to a bone so that the front end of the longitudinal second member and the cutting tip of the drill bit abut a surface of a bone or of an object; and
if required, adding an offset value stored in the digital data storage to a relative position; and
storing the relative position as a start point for measurement of the position of the cutting tip of the drill bit relative to a surface of a bone in the drilling direction with respect to time.

46. The method according to claim 45, wherein before the advancing step the following steps are performed:
positioning the surgical power drill relative to a bone so that the front end of the longitudinal second member abuts a drill sleeve inserted in soft tissue covering a bone to be treated; and
adjusting the cutting tip of the drill bit secured in engagement means of the surgical power drill relative to the longitudinal second member so that the cutting tip of the drill bit abuts a surface of a bone; and
if required, adding an offset value stored in the data storage to the relative position; and
storing the relative position as the start point for the measurement of the position of the cutting tip of the drill bit relative to a surface of a bone or of an implant in the drilling direction with respect to time.

47. The method according to claim 46, wherein before the advancing step the following steps are performed:
positioning the drill bit secured in the engagement means relative to the longitudinal second member by using a calibration device so that the front end of the second member contacts a surface of the calibration device and the cutting tip of the drill bit abuts a stop protruding from the surface of the calibration device;
storing the relative position as start point for the measurement of the position of the cutting tip of the drill bit relative to a surface of a bone or of an implant in the drilling direction with respect to time; and
positioning the surgical power drill relative to an implant so that the front end of the longitudinal second member abuts a surface of the implant.

48. The method according to claim 47, wherein the first medium penetrated by the cutting tool or drill bit of the surgical instrument is cortical or trabecular bone.

49. The surgical instrument according to claim 27, wherein the housing comprises a top part including a sterilizable window for covering the display.

50. The surgical instrument according to claim 49, wherein the part of the housing is integral with the housing and forms a casing for the display.

51. The surgical instrument according to claim 20, wherein the contactless displacement sensor comprises a reflector slideable along a drill bit and configured to abut an implant, a bone or an instrument.

52. The surgical instrument according to claim 1, wherein the similarity measure applied to select the portion of the graph which best fits the reference graph to find the position of transition in the recorded graph is a pattern recognition approach.

53. The surgical instrument according to claim 52, wherein the reference data specifies a statistical representation of a plurality of prospectively recorded graphs in the range of the transition of a cutting tool or drill bit from a first medium having a first density to a second medium having a different second density during the cutting or drilling process.

54. The surgical instrument according to claim 1, wherein the reference data are continuously amended during use of the cutting or drilling device.

55. The surgical instrument according to claim 54, wherein the reference data is amended by machine learning algorithms by involving use of a neural network.

56. The surgical instrument according to claim 1, wherein the measuring device comprises at least one accelerometer.

57. The surgical instrument according to claim 1, wherein the measuring device additionally comprises gyroscopes and/or magnetometers.

58. The surgical instrument according to claim 1, wherein the surgical instrument additionally comprises a calibration device.

59. The surgical instrument according to claim 1, wherein the processing unit is programmed to compute in real-time.

60. The surgical instrument according to claim 1, wherein the processing unit comprises a data memory to store data related to bone screw lengths, including a safety margin, screw head length, tip section length and screw length increments.

\* \* \* \* \*